United States Patent [19]

Kojima et al.

[11] Patent Number: 5,670,657

[45] Date of Patent: Sep. 23, 1997

[54] (METH) ARCYLIC ESTER DERIVATIVES

[75] Inventors: Katsunori Kojima, Higashiyamato; Yoshinori Kadoma, Meguro; Kunio Ikemura, Joyo, all of Japan

[73] Assignee: Kabushiki Kaisha Shofu, Kyoto, Japan

[21] Appl. No.: 590,174

[22] Filed: Jan. 23, 1996

Related U.S. Application Data

[62] Division of Ser. No. 378,245, Jan. 24, 1995, abandoned.

[30] Foreign Application Priority Data

Feb. 4, 1994 [JP] Japan ................................. 6-012523
Jun. 29, 1994 [JP] Japan ................................. 6-147576

[51] Int. Cl.$^6$ .................................................. C07D 339/02
[52] U.S. Cl. ........................................................ 549/39
[58] Field of Search ........................................ 549/35, 39

[56] References Cited

U.S. PATENT DOCUMENTS

| | | | |
|---|---|---|---|
| 3,513,132 | 5/1970 | Edmonds | 528/293 |
| 3,655,844 | 4/1972 | Hoyer et al. | 549/39 |
| 5,055,497 | 10/1991 | Okada et al. | 523/116 |
| 5,219,705 | 6/1993 | Kato et al. | 430/270 |
| 5,254,198 | 10/1993 | Kawa Shima et al. | 526/286 |

FOREIGN PATENT DOCUMENTS

| | | |
|---|---|---|
| 52-121858 | 1/1979 | Japan . |
| 56-120371 | 2/1983 | Japan . |
| 62-251846 | 9/1988 | Japan . |
| 62-241553 | 3/1989 | Japan . |
| 63-99116 | 10/1989 | Japan . |

OTHER PUBLICATIONS

*The Journal of the Japanese Society for Dental Materials and Devices*, vol. 5, No. 1, Jan. 1986, pp. 93–105, Katsunori Kojima, "Studies on Adhesion of Functional Monomers with SH Group to Tooth Substrates and Dental Alloys".

*The Journal of the Japanese Society for Dental Materials and Devices*, vol. 11, Special Issue 20, Sep. 1992, K. Kojima & Y. Kadoma, "Adhesive Property of precious metals treated with disulfide monomer".

*The Journal of the Japanese Society for Dental Materials and Devices*, vol. 12, Special Issue 21, Apr. 1993, K. Kojima & Y. Kadoma, "The effect of initiator on the adhesion of resin to noble metal surface treated with disulfide monomer".

Sun et al, "Ultrathin self–assembled polymeric films on solid surfaces III. Influence of acrylate dithioalkylside chair length on polymeric monolayer formation on gold", CA 121:135436 (1994).

*Primary Examiner*—José G. Dees
*Assistant Examiner*—Deborah Lambkin
*Attorney, Agent, or Firm*—Watson Cole Stevens Davis, PLLC

[57] ABSTRACT

A novel compound useful as a precious metal adhesive component is provided which can exhibit high and durable adhesivity with precious metals, such as gold, silver, platinum, and palladium, and alloys thereof. The compound is a (meth)acrylic ester derivative having a disulfide cyclic group which is represented by the general formula [I]:

$$CH_2=C(R_1)-COO-R_2-OOC-(CH_2)_4-CH\underset{S-S}{\overset{CH_2-CH_2}{<}} \quad [I]$$

in which $R_1$ represents a hydrogen atom or a methyl group, and $R_2$ represents a C1–C14 alkylene group which may have a substituent.

5 Claims, No Drawings

(METH) ACRYLIC ESTER DERIVATIVES

This is a division of application Ser. No. 08/378,245 filed Jan. 24, 1995 abandoned.

BACKGROUND OF THE INVENTION

1. Field of the Invention

The present invention relates to (meth)acrylic ester derivatives having a disulfide cyclic group. The (meth) acrylic ester derivatives may be used as precious metal adhesive components in dental and other medical industry areas, as well as in general industrial areas including the art of jewelry.

2. Description of the Prior Art

Hitherto, for use as a resin-based dental adhesive there have been known compounds which are composed principally of an instantaneously polymerized resin made up of poly(methyl methacrylate) and methyl methacrylate or a methacrylic ester called Bis-GMA resin, with a filler and a hardener used in admixture with the resin. Such compounds, as so-called dental adhesive resins, have been used for various clinical dental purposes, such as metal inlaying, onlaying, crowning and bridging, and adhesive fixation with respect to dental orthodontic brackets, metal bases, etc.

Monomers having an adhesive function which may be advantageously incorporated in Such adhesive resins are known including, for example, (meth)acrylic ester derivatives having a phosphoric group as described in Japanese Patent Application Laid-Open No. Sho 58-21607, which teaches that the (meth)acrylic ester derivatives provide improved metal adhesion.

Japanese Patent Application Laid-Open No. Sho 54-11149 discloses that 4-methacryloxyethyl trimellitate or the anhydride derivative thereof can enhance resin adhesion with metals.

However, it has been known that although the compounds disclosed in the above mentioned publications are effective for improving adhesion with non-precious metals, such as iron, aluminum, copper, tin, nickel, chromium, cobalt and titanium, and alloys thereof, their adhesion performance is very unfavorable in relation to precious metals, such as gold, silver, platinum and palladium, and alloys thereof. Therefore, from clinical points of view, it is very troublesome to carry out an electrodeposition of tin or high temperature oxidative treatment with respect to precious metals and/or their alloys, though such a way of deposition or oxidative treatment is currently in practice.

Recently, it has been proposed to provide increased adhesivity relative to precious metals by using a treating agent which contains a certain type of monomer having adhesive functions.

For example, in a dental journal *The Journal of the Japanese Society for Dental Materials and Devices*, vol. 5, pp 92–105 (1986), it is reported that a treating agent containing N-(4-mercaptophenyl)methacrylamide (hereinafter referred to as MPMA) can improve resin adhesion with any precious metal.

In Japanese Patent Application Laid-Open No. Sho 64 -83254 there is given a teaching that polymerizable double bond-containing derivatives of 1, 3, 5-triazine-2, 4-dithione and, in particular, 6-(4-vinylbenzyl-n-propyl)amino-1, 3, 5-triazine-2, 4-dithione (hereinafter referred to as VBATDT), are highly effective for improving resin adhesion with precious metals and their alloys. However, both MPMA and VBAT can only provide a very low degree of adhesion where a BPO/amine-based polymerization catalyst is used, and this poses a problem from the view point of retention of adhesion under demanding interoral conditions. Another problem is that MPMA has some deficiency in respect of storage stability.

Japanese Patent Application Laid-Open No. Sho 63-225674 teaches that polysulfide compounds, such as bis(2-methacryloyloxyalkyl) disulfide, exhibit good adhesion characteristics relative to precious metals. With primers containing such compounds, it has been found that their adhesion retentive power is very low when the primer is used in combination with general-purpose catalysts, such as benzoyl peroxide/tertiary amine, though it is recognized that the primer has some adhesion effect due to a certain polymerization catalyst which is present in an adhesive resin used in combination with the primer.

For example, in *The Journal of the Japanese Society for Dental Materials and Devices*, vol. 11, "Lecture Issue 20", pp 234–235 (1992), as well as in *The Journal of the Japanese Society for Dental Materials and Devices*, vol. 12, "Lecture Issue 21", pp 164–165 (1993), it is reported that bis(2-methacryloyloxyethyl) disulfide (hereinafter referred to as BMEDS), bis(5-methacryloyloxypentyl) disulfide (hereinafter referred to as BMPDS), and bis(10-methacryloyloxydecyl) disulfide (hereinafter referred to as BMDDS) function unfavorably in respect of adhesion with silver and silver alloys, say, 0 kgf/cm$^2$ with silver and as low as 106–289 kgf/cm$^2$ with silver alloys when benzoyl peroxide/tertiary amine catalysts are used.

In Japanese Patent Application Laid-Open No. Hei 1-268612 there is disclosed that monomers having a thiophosphoric acid group, e.g., 10-methacryloyloxy decyl dihydrogen thiophosphate (hereinafter referred to as M10PS), exhibit very good adhesion with precious metals and outstanding adhesion retentive power when the monomer is used in a proportional range of from 0.001 to 0.3 part by weight. However, monomers having a thiophosphoric acid group as represented by M10PS involve a problem objectionable from the view point of practical use such that the monomer will tend to become decomposed during storage to produce terrible odors which are extremely displeasing to the clinician when he is working for dental adhesion.

SUMMARY OF THE INVENTION

It is an object of the invention to provide a novel compound useful as a precious metal adhesive component which exhibits strong and permanent adhesion with precious metals, such as gold, silver, platinum, and palladium, without requiring the precious metals to be subjected to such pretreatment as electrodeposition of tin or oxidative treatment, and which can come into strong adhesion with any of the precious metals without being influenced by the type of polymerization catalyst used, has good storage stability and involves no generation of objectionable odors during the preparation thereof or when in use.

It is another object of the invention to provide a method for production of such a compound.

It is a further object of the invention to provide an adhesive comprising aforementioned novel compound as a precious metal adhesive component.

Accordingly, the invention relates to (meth)acrylic ester derivatives represented by the general formula [I]:

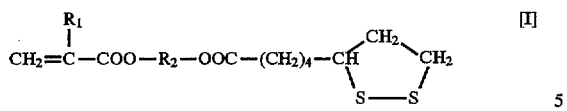

in which R₁ represents a hydrogen atom or a methyl group, and R₂ represents a C1–C14 alkylene group which may have a substituent.

DETAILED DESCRIPTION OF THE INVENTION

The present invention provides a novel (meth)acrylic ester derivative having a disulfide cyclic group which is represented by the general formula [I]:

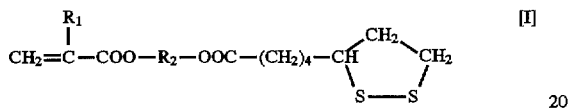

in which $R_1$ represents a hydrogen atom or a methyl group and $R_2$ represents a C1–C14 alkylene group which may have a substituent. In the present invention, the term "(meth) acrylate" means either acrylate or methacrylate.

A (meth)acrylic ester derivative represented by the general formula [I] is characterized in that it has a disulfide cyclic group within its structure. A primer or adhesive containing such a compound can solve the problems with the prior art. It exhibits strong and permanent adhesion with precious metals, such as gold, silver, platinum, and palladium, without requiring such pretreatment as electrodeposition of tin or oxidative treatment to be given to the precious metals. Further, the primer or adhesive has good storage stability and involves no generation of objectionable odors during the preparation thereof or when in use.

Because of these characteristic features thereof, (meth) acrylic ester derivatives [I] of the invention can be used as a primer component or an adhesive composition component and are therefore applicable to dental or medical adhesives as well as to jewelry and other industrial adhesives.

In the general formula [I], $R_1$ represents a hydrocarbon group having a carbon number of 1–3. A preferred $R_1$ is a hydrogen atom or a methyl group. $R_2$ represents an alkylene group having a carbon atom number of 1–30, preferably 1–14, more preferably 2–12, which may have a substituent. Substituent groups which may be bonded to $R_2$ include an unsaturated group or alkyl group, or an alkyl group bonded with a phenyl group.

Compounds represented by the general formula [I] may be specifically exemplified by those shown below.

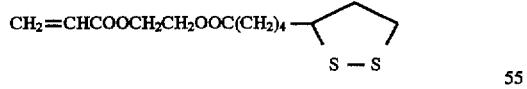

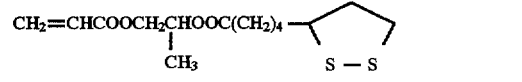

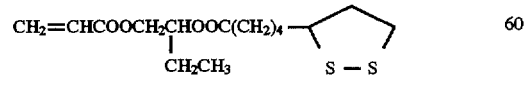

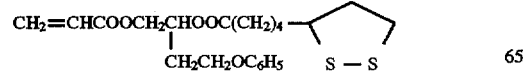

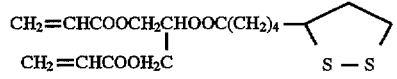

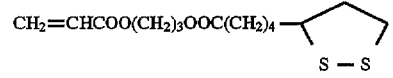

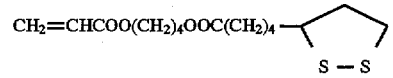

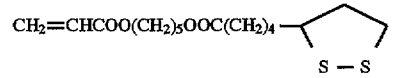

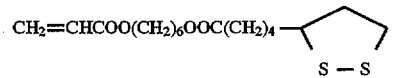

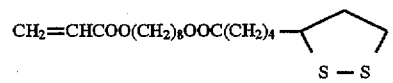

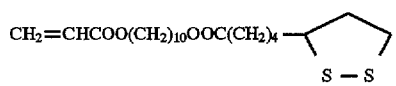

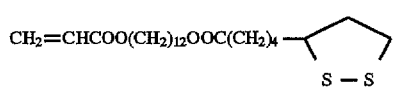

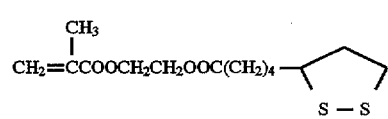

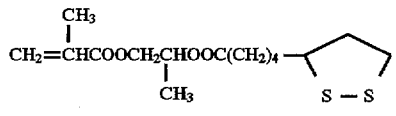

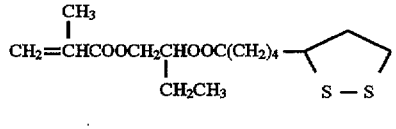

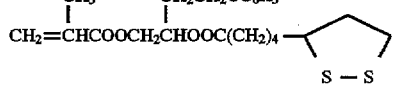

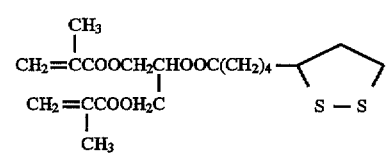

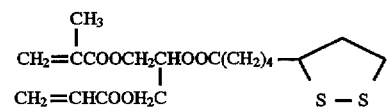

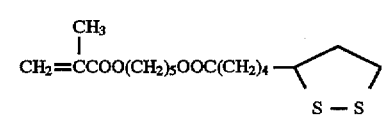

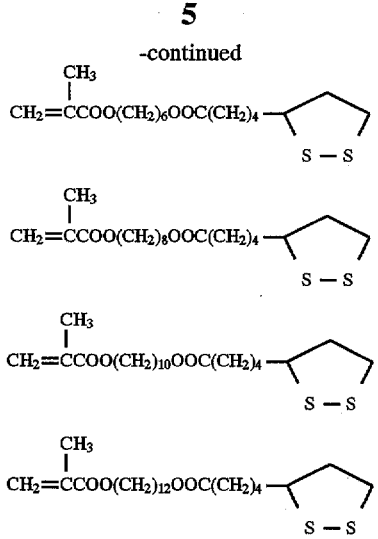

A (meth)acrylic ester derivative represented by the general formula [I] of the invention is obtainable, for example, by reacting a hydroxyalkyl (meth)acrylate compound represented by the following general formula [II] (where, $R_1$ and $R_2$ carry the same meaning as earlier defined) with a thioctic acid represented by the following formula [III]:

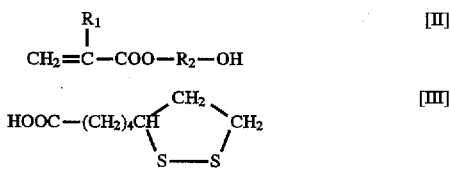

First, the method of preparing the hydroxyalkyl (meth)acrylate compound of the general formula [II] will be described.

Hydroxyalkyl (meth)acrylates represented by the general formula [II] can be easily obtained by carrying out an esterification reaction between (meth)acrylic acid and glycol, an esterification reaction between (meth)acryloyl chloride and glycol, or an epoxy ring opening reaction between (meth)acrylic acid and a compound having an epoxy group.

Useful glycols for these purposes include, for example, ethylene glycol, propylene glycol, 1, 4-butanediol, pentamethylene glycol, hexamethylene glycol, octamethylene glycol, decamethylene glycol and dodecamethylene glycol.

For purposes of esterification, acid catalysts are preferably used, including p-toluenesulfinic acid, benzenesulfonic acid, for example.

Useful compounds having an epoxy group include, for example, phenylglycidyl ether and glycidyl methacrylate. For purposes of epoxy ring opening reaction are used basic catalysts, such as pyridine, triethylamine, dimethyl-p-toluidine, and triethylbenzylammonium chloride, as well as acid catalysts including aforementioned sulfonic acids and boron trifluoride etherates.

For the purpose of preparing hydroxyalkyl (meth)acrylate represented by the general formula [II], it is preferable to use a polymerization inhibitor, such as hydroquinone, hydroquinone monomethyl ether, or butylated hydroxytoluene.

More specifically, hydroxyalkyl (meth)acrylate of the general formula [II] can be obtained by charging 1 mol to 2 mol of glycol relative to 1 mol (meth)acrylic acid, and 2 to 5 wt % of acid catalyst relative to the total charge, adding a small amount of a polymerization inhibitor, and carrying out a reaction under normal pressure or reduced pressure at a temperature of not more than 130° C.

Alternatively, such a compound may be obtained by charging 1 mol to 1.5 mol of glycol and 1 mol of tertiary amine (e.g., pyridine or triethylamine), as a dehydrohalogenation agent, in the presence of a solvent, and gradually adding 1 mol of (meth)acrylic chloride dropwise at a temperature of not more than ordinary temperature thereby to develop an esterification reaction.

In these cases, a hydroxyalkyl (meth)acrylate monoester and an alkylene (meth)acrylate diester are obtained as products. The hydroxyalkyl (meth)acrylate can be separated and purified by distillation or column chromatography.

It is also possible to obtain such compound by carrying out an equimolar reaction between glycidyl methacrylate and (meth)acrylic acid using tertiary amine as a catalyst.

Then, the method for preparation of (meth)acrylic ester derivatives of the general formula [I] will be described.

A (meth)acrylic ester derivative represented by the general formula [I] can be obtained by charging 0.5 to 1.5 mol, preferably 1.0 mol, of thioctic acid represented by the formula [III], relative to 1 mol of hydroxyalkyl (meth) acrylate represented by the general formula [II], and carrying out an esterification reaction under a solventless condition or in an inert solvent, in the presence of a catalyst.

Useful catalysts for esterification include, for example, p-toluenesulfonic acid, benzenesulfonic acid and N, N'-dicyclohexylcarbodiimide. Useful inert solvents include, for example, benzene, toluene and xylene.

Reaction may be carried out at a temperature of not more than 120° C. under normal pressure or reduced pressure. The reaction product is diluted with a solvent, such as ethyl ether, benzene, ethyl acetate or chloroform, followed by water washing, and is thus made free from unreacted matter and by-product.

The resulting product is then subjected to dehydration/concentration with anhydrous sodium sulfate, and the concentrate is passed through a silica gel column, with an inert solvent used as a developing solvent, for separation and refinement, through which process can be directly obtained compounds of the invention.

High-purity cyclic disulfide compounds [I] obtained through the process of separation and refinement are, in most cases, in the form of either a yellowish clear viscous fluid or yellow crystal.

The (meth)acrylic ester derivatives of the invention are applicable to various kinds of adhesive compositions curable by radical polymerization.

The "adhesive compositions" herein are applicable to dental primers, dental adhesives, dental cement, dental sealants, dental composite fillers, hard resin coronal adhesives, general industrial adhesives, industrial art adhesives, jewelry adhesives, paints, space fillers, etc.

An adhesive composition of the invention comprises (a) compound [I] of the invention, and at least one of the following components: (b) organic solvent, (c) radical polymerizable monomer, and (d) polymerization catalyst.

The adhesive compositions of the invention are not only available for use as primers, but also may be used as adhesives of the type which can be cured at room temperature, or upon exposure to light, or by heating, so that they provide for strong adhesion with precious metals and non-precious metals in particular, and also allow good adhesion with dentin and ceramics. Such composition need not necessarily be of the one-pack type. It may be of such other type as two-pack type, powder/liquid type, paste & paste type, or one-paste type.

Organic solvents useful as component (b) above include, for example, methyl alcohol, ethyl alcohol, ethyl acetate, chloroform, methylethyl ketone, acetone, benzene, toluene and xylene. Acetone is preferred.

The mixing ratio of component (a) to component (b) may be suitably varied according to the intended purpose of the composition, but generally it may be selected so that the weight ratio of component (a)/component (b) will come within the range of from 1/10,000 to 1/5, preferably from 1/5,000 to 1/500. If the weight ratio is lower than 1/10000, or higher than 1/5, the composition will become unacceptably lowered in its adhesive quality for use as an adhesive or an adhesive primer.

Radical polymerizable monomers useful as component (c) above include, for example, vinyl acetate, acrylonitrile, styrene, (meth)acrylic acid; (meth)acrylates, such as methyl (meth)acrylate and ethyl (meth)acrylate, and their substitution compounds with hydroxyl- or halogen-substituted alkyl side chains; methoxydiethylene glycol (meth)acrylate, methoxypolyethylene glycol (meth)acrylate, methoxypolyethylene glycol (meth)acrylate, ethylene glycol di(meth)acrylate, triethylene glycol di(meth)acrylate, tetraethylene glycol di(meth)acrylate, hexamethylene glycol di(meth)acrylate, polyethylene glycol di(meth)acrylate, propylene glycol di(meth)acrylate, polypropylene glycol di(meth)acrylate, neopentyl glycol di(meth)acrylate, 2, 2'-bis{4-(meth)acryloxypropoxyphenyl} propane, 2, 2'-bis{4-(meth)acryloxyethoxyphenyl} propane, 2, 2'-bis{4-(meth)acryloxydiethoxyphenyl} propane, bisphenol A di(meth)acrylate, bisphenol A diglycidyl (meth)acrylate, trimethylolpropane tri(meth)acrylate, trimethylolethane tri(meth)acrylate, tetramethylolethane tetra(meth)acrylate, epoxy (meth)acrylate; urethane (meth)acrylates as reaction products of organic diisocyanates with (meth)acrylic oxyalkyl; polymerizable prepolymers which are reaction products of urethane prepolymers (reaction products of organic diisocyanates with diol) and a (meth)acrylic ester of an oxyalkanol having at least two carbon atoms, and which include at least two polymerizable ethylenic unsaturated groups; and reaction products of dibasic carboxylic acid having an ethylenic unsaturated group with bivalent alcohol (which are generally polyesters having an ethylenic unsaturated group), or polymerizable monomers having a silanol group, such as γ-methacryloxypropyltrimethoxysilane.

These radical polymerizable compounds may be used alone or in combination. Polymerizable monomers, such as methyl (meta)acrylate or di(meth)acrylate, are preferably used in combination with polymerizable prepolymers, such as 2, 2'-bis{4-(meth)acryloxypropoxyphenyl}propane or urethane (meth)acrylate.

The mixing ratio of component (a) to component (c) may be suitably varied according to the intended purpose of the composition, but generally it may be selected so that the weight ratio of component (a)/ component (c) will come within the range of from 1/10,000 to 1/5, preferably from 1/5,000 to 1/500. If the weight ratio is lower than 1/10,000, or higher than 1/5, the composition will become unacceptably lowered in its adhesive quality for use as an adhesive or an adhesive primer.

Polymerization catalysts useful as component (d) include, for example, peroxides, such as benzoyl peroxide, 4, 4'-dichlorobenzoyl peroxide, and dicumyl peroxide; and azobisisobutyronitrile. When polymerization is carried out at room temperature, any of the following combinations is preferred: tri-n-butylborane, cobalt naphthenate/methylethyl peroxide, aromatic tertiary amine/benzoyl peroxide, barbituric acid derivative/copper ion/halogenated compound, aromatic sulfinic acid (or salt thereof)/aromatic tertiary amine/diacyl peroxide, barbituric acid derivative/aromatic tertiary amine/diacyl peroxide, aromatic sulfinic acid (or salt thereof)/aromatic tertiary amine/t-butyl peroxymaleic acid, and aromatic sulfinyl amide/aromatic tertiary amine/t-butyl peroxymaleic acid.

The aromatic tertiary amine is selected from among dimethylaniline, dimethyl-p-toluidine, N, N-di(2-hydroxyethyl)-p-toluidine, etc. which are conventionally used as such.

The aromatic sulfinic acid (or salt thereof) is selected from among benzene sulfinic acid, sodium benzenesulfinate, sodium p-toluenesulfinate, etc. which are conventionally used as such.

The barbituric acid derivative is selected from among 5-butyl barbituric acid, 1, 3, 5-trimethyl-barbituric acid, 1-benzyl-5-phenyl barbituric acid, 1-cyclohexyl-5-ethyl barbituric acid, thiobarbituric acid derivative, etc. which are conventionally used as such.

The aromatic sulfinyl amide is selected from among N, N-dimethyl-p-toluenesulfinyl amide, benzene sulfinyl amide, N, N-dimethyl-p-toluenesulfinic acid morpholide, etc. which are conventionally used as such.

When polymerization is carried out through exposure to ultraviolet rays or visible light rays, a photosensitizer and an accelerator, respectively of conventional types, are preferably used in combination.

The photosensitizer is selected from among benzoin, benzoin alkyl ethers, thioxanthone, benzyl, camphor quinone and derivatives thereof, α-diketone, etc.

The accelerator is selected from among the following compounds: N-methyl diethanolamine, N, N-dimethylaminoethyl methacrylate, N, N-diethylaminoethyl methacrylate, tributyl phosphine, aryl thiourea; organic tin compounds, including di-n-butyl-tin-malate, di-n-butyl-tin-malate (polymer), di-n-octyl-tin-malate, di-n-octyl-tin-malate (copolymer), di-n-octyl-tin-laurate, and di-n-butyl-tin-dilaurate; 5-butyl barbituric acid, 1, 3, 5-trimethyl barbituric acid, 1-benzyl-5-phenyl barbituric acid, 1-cyclohexyl-5-ethyl barbituric acid, and thiobarbituric acid derivatives.

The amount of use of such (d) component may be usually selected within the range of from about 0.1% to 5% (wt %, same applies hereinafter) relative to the total of component (a) and component (b): or of component (a) and component (c).

An adhesive composition of the invention comprises aforesaid component (a) as an essential ingredient, and other ingredient or ingredients suitably selected from components (b) through (d). Further, according to the purpose for which the adhesive composition is used (such as adhesive, dental cement, dental composite filler, coronal hard resin adhesive, paint, and space filler), conventional additive ingredients, e.g., inorganic and organic fillers, modifying agents, thickeners, dyes, pigments, polymerization regulators and polymerization inhibitors, may be selectively admixed in suitable quantities.

For example, for use as inorganic and organic fillers may be enumerated: organic polymer powders of poly(methyl methacrylate), poly(ethyl methacrylate), methyl methacrylate/ethyl methacrylate copolymer, polystyrene, etc.; organic fillers prepared by grinding hardened thermosetting resin material or such resin material including inorganic filler material; inorganic fillers (kaolin, talc, quartz, silica, colloidal silica, alumina, aluminosilicate, silicon nitride, barium sulfate, calcium phosphate, glass powder, etc.); and composite fillers made up of inorganic and organic fillers. Such fillers are suitable for the purpose of using the composition in a powder/liquid form, or in a paste form, or in a slurry form. For use as polymerization inhibitor may be exemplified hydroquinone, hydroquinone monomethylether,

EXAMPLE 1

Into a four-necked 500 ml flask were introduced 6.50 g (0.05 mol) of 2-hydroxyethyl methacrylate, 10.30 g (0.05 mol) of N, N'-dicyclohexylcarbodiimide, 10.36 g (0.05 mol) of thioctic acid(=6, 8-dithiooctanoic acid), and 100 g of benzene, which were dissolved therein, and the solution was continuously stirred at room temperature for two weeks. As reaction progressed, there developed a precipitate of white color. After completion of the reaction, the precipitate was filtered. Benzene was distilled away from the resulting filtrate under reduced pressure in order to concentrate the filtrate. The concentrate was subjected to the process of separation and purification by a silica gel column using benzene as a developing solvent. As a result, an object compound in the form of a yellowish transparent viscous liquid was obtained in the amount of 6.09 g (yield:38.24%).

Analyses of the compound, including $^1$H-NMR spectral analysis, $^{13}$C-NMR spectral analysis and mass spectral analysis, were carried out. As a result, the compound was identified as 2-methacryloyloxyethyl 6, 8-dithiooctanate (referred to as 2-MEDT) represented by the following formula.

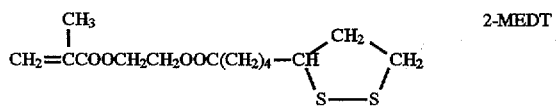

2-MEDT $^1$H-NMR spectrum:(ppm)

| | |
|---|---|
| 1.47, 1.67, 2.35, 3.14 | (8H —OOC—(C$\underline{H}_2$)$_4$—) |
| 1.95 | (3H —C$\underline{H}_3$) |
| 1.67, 1.91, 2.46, 3.56 | (5H >C$\underline{H}$—C$\underline{H}_2$—C$\underline{H}_2$—) |
| 4.35 | (4H —COO—$\underline{C}$H$_2$—$\underline{C}$H$_2$—OOC—) |
| 5.60, 6.13 | (2H C$\underline{H}_2$=C<) |
| [0066] | |

$^{13}$C-NMR spectrum:(ppm)

| | |
|---|---|
| 18.1 | (1C —$\underline{C}$H$_3$) |
| 24.5, 28.6, 33.7, 34.5 | (4C —OO$\underline{C}$—($\underline{C}$H$_2$)$_4$—) |
| 38.4, 40.1, 56.2 | (3C >$\underline{C}$H—$\underline{C}$H$_2$—$\underline{C}$H$_2$—) |
| 61.9, 62.3 | (2C —COO—$\underline{C}$H$_2$—$\underline{C}$H$_2$—OOC—) |
| 125.9, 135.8 | (2C $\underline{C}$H$_2$=$\underline{C}$<) |
| 166.9, 173.0 | (2C —$\underline{C}$OO—CH$_2$—CH$_2$—OO$\underline{C}$—) |
| [0067] | |

MASS spectrum:molecular weight 318

EXAMPLE 2

Into a four-necked 2-liter flask were introduced 236 g (2 mol) of 1, 6-hexamethyleneglycol, 118 g (1.5 mol) of pyridine, and 1200 g of tetrahydrofuran. The mixture was cooled to a temperature lower than 10° C. By using a dropping funnel 157 g (1.5 mol) of methacryloyl chloride was gradually added dropwise in 2 to 3 hours so as not to allow the interior temperature to go higher than 15° C., thereby causing a reaction. After completion of the dropping, further reaction was made at a temperature of not more than 15° C. for 4 hours.

Separated hydrochloride was removed and solvent was distilled away at 40° C. under a reduced pressure of 40 mmHg. The residue obtained was diluted with 500 ml of ethyl ether. This ether solution was washed twice with 500 ml of aqueous solution and was then washed with a 5% aqueous solution of sodium carbonate. Further the solution was washed with 400 ml of water four times. The ether layer was dehydrated with anhydrous magnesium sulfate and solvent was distilled away at 35° C. under a reduced pressure of 40 mmHg. As a result, a yellow-colored oily residue was obtained in the amount of 150 g. From this oily residue was separated by column chromatography a colorless, transparent viscous liquid 6-hydroxyhexyl methacrylate in the amount of 70 g.

Into a four-necked 500 ml flask were introduced 13.0 g (0.07 mol) of 6-hydroxyethyl methacrylate, 10.30 g (0.05 mol) of N, N'-dicyclohexylcarbodiimide, 10.36 g (0.05 mol) of thioctic acid and 100 g of benzene, which were dissolved therein. The solution was continuously stirred at room temperature for two weeks. There developed a white precipitate. After completion of the reaction, the precipitate was filtered.

Subsequently, the step of separation and purification was carried out in the same manner as in EXAMPLE 1. Thus an object compound in the form of a yellowish transparent viscous liquid was obtained in the amount of 6.10 g (yield: 32.62%). Analyses of the compound, including $^1$H-NMR spectral analysis, $^{13}$C-NMR spectral analysis and mass spectral analysis, were carried out. As a result, the compound was identified as 6-methacryloyloxyhexyl 6, 8-dithiooctanate (referred to as 6-MHDT) represented by the following formula.

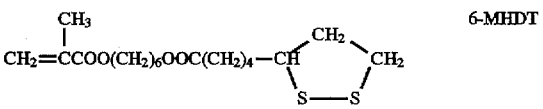

6-MHDT $^1$H-NMR spectrum:(ppm)

| | |
|---|---|
| 1.34, 1.44, 1.67 | (8H —COO—CH$_2$—(C$\underline{H}_2$)$_4$—CH$_2$—OOC—) |
| 1.34, 1.67, 2.32, 3.15 | (8H —OOC—(C$\underline{H}_2$)$_4$—C$\underline{H}$<) |
| 1.94 | (3H —C$\underline{H}_3$) |
| 2.47, 1.67, 1.91, 3.57 | (5H >C$\underline{H}$—C$\underline{H}_2$—C$\underline{H}_2$—) |
| 4.06, 4.14 | (4H —O—C$\underline{H}_2$—(CH$_2$)$_4$—C$\underline{H}_2$—O—) |
| 5.55, 6.09 | (2H C$\underline{H}_2$=C<) |

$^{13}$C-NMR spectrum:(ppm)

| | |
|---|---|
| 18.1 | (1C —$\underline{C}$H$_3$) |
| 24.5, 28.5, 33.9, 34.4 | (4C —OO$\underline{C}$—($\underline{C}$H$_2$)$_4$—) |
| 38.2, 40.0, 56.1 | (3C >$\underline{C}$H—$\underline{C}$H$_2$—$\underline{C}$H$_2$—) |
| 25.4, 25.6, 28.9, 28.4, 64.1, 64.5 | (6C —O—($\underline{C}$H$_2$)$_6$—O—) |
| 124.9, 136.3 | (2C $\underline{C}$H$_2$=$\underline{C}$<) |
| 167.2, 173.2 | (2C —$\underline{C}$OO—(CH$_2$)$_6$—OO$\underline{C}$—) |

MASS spectrum:molecular weight 374

EXAMPLE 3

Into four-necked 1-liter flask were introduced 349 g (2 mol) of 1, 10-decamethylene glycol, 103 g (1.2 mol) of methacrylic acid, 9 g of p-toluenesulfonic acid, and 0.5 g each of 2, 2'-methylenebis(4-ethyl-6-tert-butylphenol) and butylated hydroxytoluene, which were heated and stirred for 5 hours at 90°–110° C. under a reduced pressure of 70–100 mmHg, being thereby caused to react with each other.

After the reaction, the step of separation and purification was carried out in the same way as in EXAMPLE 2 to give 100 g of 10-hydroxydecyl methacrylate, a colorless, transparent viscous liquid.

Into a four-necked 500 ml flask were introduced 16.94 g (0.07 mol) of 10-hydroxydecyl methacrylate, 10.30 g (0.05 mol) of N, N'-dicyclohexylcarbodiimide, 10.36 g (0.05 mol) of thioctic acid (6, 8-dithiooctanoic acid), and 100 g of benzene, which were dissolved therein. The solution was continuously agitated at room temperature for two weeks. There developed a white precipitate. After completion of the reaction step, the precipitate was filtered.

Subsequently, the step of separation and purification was carried out in the same manner as in EXAMPLE 1. Thus an object compound in the form of a yellowish transparent viscous liquid was obtained in the amount of 7.10 g (yield: 33.02%).

Analyses of the compound, including $^1$H-NMR spectral analysis, $^{13}$C-NMR spectral analysis and mass spectral analysis, were carried out. As a result, the compound was identified as 10-methacryloyloxydecyl 6, 8-dithiooctanate (referred to as 10-MDDT) represented by the following formula.

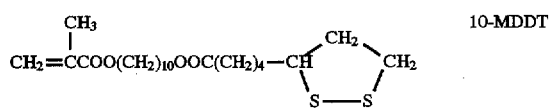

10-MDDT $^1$H-NMR spectrum:(ppm)

| | |
|---|---|
| 1.30 | (12H —O—CH$_2$CH$_2$—(C$\underline{H_2}$)$_6$—CH$_2$CH$_2$—O—) |
| 1.66, 1.46 | (4H —O—CH$_2$C$\underline{H_2}$—(CH$_2$)$_6$—C$\underline{H_2}$CH$_2$—O—) |
| 1.30, 1.66, 2.32, 3.15 | (8H —OOC—(C$\underline{H_2}$)$_4$—CH<) |
| 1.94 | (3H —C$\underline{H_3}$) |
| 1.66, 1.92, 2.46, 3.57 | (5H <C$\underline{H}$—C$\underline{H_2}$—C$\underline{H_2}$—) |
| 4.06, 4.13 | (4H —O—C$\underline{H_2}$CH$_2$—(CH$_2$)$_6$—CH$_2$C$\underline{H_2}$—O—) |
| 5.55, 6.09 | (2H C$\underline{H_2}$=C<) |

$^{13}$C-NMR spectrum:(ppm)

| | |
|---|---|
| 18.2 | (1C —$\underline{C}$H$_3$) |
| 24.6, 28.6, 34.0, 34.5 | (4C —OO$\underline{C}$—($\underline{C}$H$_2$)$_4$—) |
| 38.3, 40.1, 56.2 | (3C >$\underline{C}$H—$\underline{C}$H$_2$—$\underline{C}$H$_2$—) |
| 28.5, 28.6, 28.8, 25.8, 29.1, 29.3, 64.3, 64.6 | (10C —O—($\underline{C}$H$_2$)$_{10}$—O—) |
| 124.9, 136.4 | (2C $\underline{C}$H$_2$=$\underline{C}$<) |
| 167.3, 173.4 | (2C —$\underline{C}$OO—(CH$_2$)$_{10}$—OO$\underline{C}$—) |

MASS spectrum:molecular weight 430

EXAMPLE 4

Into a four-necked 500 ml flask were introduced 9.2 g (0.08 mol of 2-hydroxyethyl acrylate, 10.30 g (0.05 mol) of N, N'-dicyclohexylcarbodiimide, 10.36 g (0.05 mol) of thioctic acid and 100 g of benzene, which were dissolved therein. The solution was continuously stirred at room temperature for two weeks. There developed a white precipitate. After completion of the reaction step, the precipitate was filtered.

Subsequently, the step of separation and purification was carried out in the same manner as in EXAMPLE 1. Thus an object compound in the form of a yellow viscous liquid was obtained in the amount of 5.98 g (yield: 39.34%).

Analyses of the compound, including $^1$H-NMR spectral analysis, $^{13}$C-NMR spectral analysis and mass spectral analysis, were carried out. As a result, the compound was identified as 2-acryloyloxyethyl 6, 8-dithiooctanate (referred to as 2-AEDT) represented by the following formula.

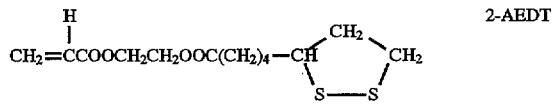

2-AEDT $^1$H-NMR spectrum:(ppm)

| | |
|---|---|
| 1.48, 1.68, 2.36, 3.15 | (8H —OOC—(C$\underline{H_2}$)$_4$—) |
| 1.68, 1.90, 2.46, 3.56 | (5H >C$\underline{H}$—C$\underline{H_2}$—C$\underline{H_2}$—) |
| 4.35 | (4H —COO—C$\underline{H_2}$—C$\underline{H_2}$—OOC—) |
| 5.87, 6.15, 6.44 | (3H C$\underline{H_2}$=C$\underline{H}$—) |

$^{13}$C-NMR spectrum:(ppm)

| | |
|---|---|
| 24.4, 28.5, 33.7, 34.4 | (4C —OO$\underline{C}$—($\underline{C}$H$_2$)$_4$—) |
| 38.3, 40.1, 56.2 | (3C >$\underline{C}$H—$\underline{C}$H$_2$—$\underline{C}$H$_2$—) |
| 173.0, 165.7 | (2C —$\underline{C}$OO—CH$_2$—CH$_2$—OO$\underline{C}$—) |
| 127.9, 131.2 | (2C $\underline{C}$H$_2$=$\underline{C}$<) |
| 62.1, 61.9 | (2C —COO—$\underline{C}$H$_2$—$\underline{C}$H$_2$—OOC—) |

MASS spectrum:molecular weight 304

EXAMPLE 5

Into a four-necked 500 ml flask were introduced 10.32 g (0.08 mol) of 2-hydroxypropyl acrylate, 10.30 g (0.05 mol) of N, N'-dicyclohexylcarbodiimide, 10.36 g (0.05 mol) of thioctic acid and 100 g of benzene which were dissolved therein, and the solution was continuously stirred at room temperature for two weeks. There developed a white precipitate. After completion of the reaction step, the precipitate was filtered.

Subsequently, the step of separation and purification was carried out in the same manner as in EXAMPLE 1. Thus an object compound in the form of a light yellow, transparent viscous liquid was obtained in the amount of 4.63 g (yield: 29.11%).

Analyses of the compound, including $^1$H-NMR spectral analysis, $^{13}$C-NMR spectral analysis and mass spectral analysis, were carried out. As a result, the compound was identified as 1-methyl-2-acryloyloxyethyl 6, 8-dithiooctanate (referred to as MAEDT) represented by the following formula.

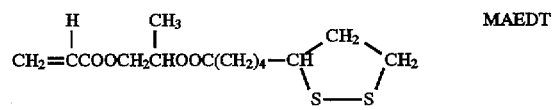

MAEDT $^1$H-NMR spectrum:(ppm)

| | |
|---|---|
| 1.47, 1.66, 2.32, 3.14 | (8H —OOC—(C$\underline{H_2}$)$_4$—) |
| 1.66, 1.90, 2.45, 3.56 | (5H >C$\underline{H}$—C$\underline{H_2}$—C$\underline{H_2}$—) |
| 4.18, 5.20 | (3H —COO—C$\underline{H_2}$—C$\underline{H}$—OOC—) |
| 5.84, 6.06, 6.40 | (3H C$\underline{H_2}$=C$\underline{H}$—) |
| 1.28 | (3H —CH$_2$—CH(C$\underline{H_3}$)—) |

$^{13}$C-NMR spectrum:(ppm)

| | |
|---|---|
| 24.4, 28.4, 33.4, 34.3 | (4C —OO$\underline{C}$—($\underline{C}$H$_2$)$_4$—) |
| 38.2, 40.0, 56.0, | (3C >$\underline{C}$H—$\underline{C}$H$_2$—$\underline{C}$H$_2$—) |
| 16.3, 65.6, 68.2 | (3C —$\underline{C}$OO—$\underline{C}$H$_2$—$\underline{C}$H(CH$_3$)—OOC—) |
| 128.2, 130.7 | (2C $\underline{C}$H$_2$=$\underline{C}$<) |
| 165.2, 172.8 | (2C —$\underline{C}$OO—CH$_2$—CH(CH$_3$)—OO$\underline{C}$—) |

MASS spectrum:molecular weight 318

EXAMPLE 6

Into a four-necked 500 ml flask were introduced 12.64 g (0.08 mol) of 2-hydroxybutyl methacrylate, 10.30 g (0.05 mol) of N, N'-dicyclohexylcarbodiimide, 10.36 g (0.05 mol) of thioctic acid and 100 g of benzene, which were dissolved therein. The solution was continuously stirred at room temperature for two weeks. There developed a white precipitate. After completion of the reaction step, the precipitate was filtered.

Subsequently, the step of separation and purification was carried out in the same manner as in EXAMPLE 1. Thus an object compound in the form of a light yellow viscous liquid was obtained in the amount of 3.50 g (yield: 20.45%).

Analyses of the compound, including $^1$H-NMR spectral analysis, $^{13}$C-NMR spectral analysis and mass spectral analysis, were carried out. As a result, the compound was identified as 1-ethyl-2-methacryloyloxyethyl 6, 8-dithiooctanate (referred to as EMEDT) represented by the following formula.

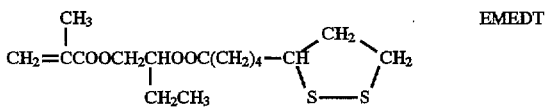

$^1$H-NMR spectrum analysis:(ppm)

| | |
|---|---|
| 1.46, 1.59~1.73, 2.32, 3.14 | (8H —OOC—(CH$_2$)$_4$—) |
| 1.59~1.73, 1.91, 2.46, 3.56 | (5H —CH—CH$_2$—CH$_2$<) |
| 4.26, 4.13, 5.08 | (3H —COO—CH$_2$—CH—OOC—) |
| 0.95, 1.59~1.73 | (5H —CH$_2$—CH$_3$) |
| 5.58, 6.11 | (2H H$_2$C=C<) |
| 1.95 | (3H =C(CH$_3$)—) |

$^{13}$C-NMR spectrum:(ppm)

| | |
|---|---|
| 18.2 | (1C —CH$_3$) |
| 24.6, 28.6, 33.8, 34.5 | (4C —OOC—(CH$_2$)$_4$<) |
| 38.4, 40.1, 56.2 | (3C >CH—CH$_2$—CH$_2$—) |
| 64.5, 72.9 | (2C —COO—CH$_2$—C(-)H—OOC—) |

("-C(-)H-" represents a secondary carbon atom hereinafter.)

| | |
|---|---|
| 125.5, 136.2 | (2C CH$_2$=C<) |
| 166.8, 173.0 | (2C —COO—CH$_2$—C(-)H—OOC—) |
| 9.3, 23.8 | (2C —CH$_2$—CH$_3$) |

MASS spectrum:molecular weight 346

EXAMPLE 7

Into a three-necked 500-ml flask were introduced 172 g (2.0 mol) of methacrylic acid, 298 g (2.1 mol) of glycidyl methacrylate, 2.4 g of triethylamine and 0.02 g of butylated hydroxytoluene, and they were caused to react with each other by being stirred at a reaction temperature of 68° C. for 12 hours. As a result, a viscous liquid was obtained.

The viscous liquid was repetitively subjected to washing and drying in substantially the same manner as in EXAMPLE 2. A colorless, transparent viscous liquid 1, 3-di(methacryloxy)-2-hydroxypropane was obtained quantitatively.

Into a four-necked 500-ml flask were introduced 16.2 (0.07 mol) of 1, 3-di(methacryloxy)-2-hydroxypropane, 10.30 g (0.05 mol) of N, N'-dicyclohexyl-carbodiimide, 10.36 g (0.05 mol) of thioctic acid and 100 g of benzene, which were dissolved therein. The solution was continuously stirred at room temperature for two weeks. There developed a white precipitate. After completion of the reaction step, the precipitate was filtered.

The step of separation and purification was carried out in the same manner as in EXAMPLE 1. Thus an object compound in the form of a yellow, transparent viscous liquid was obtained in the amount of 3.38 g (yields: 16.09%).

Analyses of the compound, including $^1$H-NMR spectral analysis, $^{13}$C-NMR spectral analysis and mass spectral analysis, were carried out. As a result, the compound was identified as bis(methacryloyloxymethyl)methyl 6, 8-dithiooctanate (referred to as BMMMDT) represented by the following formula.

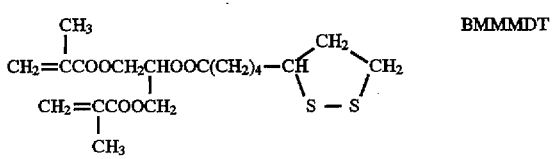

$^1$H-NMR spectrum:(ppm)

| | |
|---|---|
| 1.94 | (6H (CH$_2$=C(CH$_3$)—COOCH$_2$)$_2$—CH—) |
| 5.60, 6.12 | (4H (CH$_2$=C(CH$_3$)—COOCH$_2$)$_2$—CH—) |
| 4.37 | (4H (CH$_2$=C(CH$_3$)—COOCH$_2$)$_2$—CH—) |
| 5.43 | (1H (CH$_2$=C(CH$_3$)—COO—CH$_2$)$_2$—CH—) |
| 1.48, 1.66, 2.35, 3.13 | (8H —OOC—(CH$_2$)$_4$—) |
| 1.66, 1.90, 2.46, 3.56 | (5H >CH—CH$_2$—CH$_2$—) |

$^{13}$C-NMR spectrum analysis:(ppm)

| | |
|---|---|
| 126.3, 135.6 | (4C (CH$_2$=C(CH$_3$)—COOCH$_2$)$_2$CH—) |
| 18.1 | (2C (CH$_2$=C(CH$_3$)—COOCH$_2$)$_2$—CH—) |
| 62.4, 173.0 | (4C (CH$_2$=C(CH$_3$)COOCH$_2$)$_2$—CH—) |
| 69.2 | (1C (CH$_2$=C(CH$_3$)—COOCH$_2$)$_2$—CH—) |
| 24.5, 28.6, 33.8, 34.5 | (4C —OOC—(CH$_2$)$_4$—) |
| 166.6 | (1C —OOC—(CH$_2$)$_4$—) |
| 38.4, 40.1, 56.2 | (3C >—CH—CH$_2$—CH$_2$—) |

MASS spectrum:molecular weight 420

EXAMPLES 8–14 AND COMPARATIVE EXAMPLES 1, 2

Compounds according to the present invention were evaluated as to their adhesion performance relative to precious metals and alloys thereof. In connection with these evaluations, seven kinds of acetone solutions were prepared which respectively contain 5.0% of corresponding ones of the (meth)acrylic ester derivatives synthesized in EXAMPLES 1 through 7, namely, 2-methacryloyloxyethyl 6, 8-dithiooctanate (2-MEDT), 6-methacryloyloxyhexyl 6, 8-dithiooctanate (6-MHDT), 10-methacryloyloxydecyl 6, 8-dithiooctanate (10-MDDT), 2-acryloyloxyethyl 6, 8-dithiooctanate (2-AEDT), 1-methyl-2-acryloyloxyethyl 6, 8-dithiooctanate (MAEDT), 1-ethyl-2-methacryloyloxyethyl 6, 8-dithiooctanate (EMEDT) and bis (methacryloyloxymethyl)methyl 6, 8-dithiooctanate (BMMMDT). The respective acetone solutions were used as primers.

In conducting necessary experiments, initially the surface of each metal substrate was abrasively finished with alumina sand paper No. #4000. Then a specifically prepared primer comprising one of the compounds of the invention was coated on the substrate surface. The treated metal substrate sample was ultrasonically cleaned in acetone and allowed to stand overnight in acetone.

Subsequently, the sample was ultrasonically further cleaned in acetone and then dried. Thereafter, with respect to the substrate sample, an area for adhesion was defined by means of a cellophane tape having perforations of 5 mm diameter each.

Poly(methyl methacrylate) (PMMA) and methyl methacrylate (MMA) were used as adhesive resins, and in conjunction with these resins, partially oxidated tri-n-butylborane (TBBO) was used as a polymerization catalyst. In effect, therefore, primer-surfaced metals were brought into bond by using MMA-PMMA/TBBO system resins for adhesion.

For evaluation of bonded samples as to their bond durability, the bonded samples were subjected to 2,000-time thermal cycle tests in which they were immersed in water at 4° C. and at 60° C. in alternate one-minute intervals.

Subsequently, tensile bond strength measurements were made by using "Shimazu Autograph Model AGS-1000A" under the conditions of crosshead speed 2 mm/min. Measurements were made of the strength of bond between metals of same kind, except that only where pure gold was involved, bond strength between pure gold and stainless steel rod was measured.

For comparison purposes, bonded samples in which respective metal substrates were not subjected to primer coating and conventional 4-methacryloxyethyl trimellitate anhydride (4-META) was used instead of a compound of the invention were also tested in the same way as above described. The results the foregoing tests are shown in Table 1.

TABLE 1

Metal-Metal Tensile Bond Strength (kgf/cm$^2$) in 2000-Time Thermal Cycle Tests: TBBO system

| Substrate Metal | EXAMPLE | | | | | | | COMPARATIVE EXAMPLE | |
|---|---|---|---|---|---|---|---|---|---|
| | 8 (2-MEDT) | 9 (6-MHDT) | 10 (10-MDDT) | 11 (2-AEDT) | 12 (MAEDT) | 13 (EMEDT) | 14 (BMMMDT) | 1 (4-META) | 2 (NONE) |
| Gold | 176 | 252 | 299 | 263 | 265 | 252 | 187 | 35 | 0 |
| Silver | 445 | 506 | 488 | 476 | 477 | 464 | 455 | 65 | 0 |
| Platinum | 486 | 475 | 482 | 485 | 442 | 453 | 375 | 79 | 0 |
| Palladium | 430 | 434 | 424 | 374 | 412 | 406 | 403 | 104 | 0 |
| Gold alloy | 347 | 494 | 479 | 396 | 474 | 470 | 427 | 154 | 0 |
| Silver alloy | 397 | 506 | 432 | 307 | 351 | 346 | 248 | 32 | 0 |
| Gold/silver/palladium alloy | 416 | 438 | 490 | 357 | 498 | 443 | 417 | 199 | 32 |

Notes:
Adhesive resins used: MMA—PMMA/TBBO resin system.
Precious metals: all in pure state; alloys used: alloys for dental
Gold alloy: "Casting Gold M. C." (type IV) (made by GC K. K.)
Silver alloy: "Sunsilver C. B." (made by Sankin K. K.)
Gold/silver/palladium alloy: "Castwell M. C."(made by GG K. K.)

EXAMPLE 15 AND COMPARATIVE EXAMPLES 3–8

2-methacryloyloxyethyl 6, 8-dithiooctanate (2-MEDT), a (meth)acrylic ester derivative of the invention, and conventional adhesive monomers including 4-methacryloxyethyl trimellitate anhydride (4-META), 6-(4-vinylbenzyl-n-propyl)amino-1, 3, 5-triazine-2, 4-dithion (VBATDT), N-(4-mercaptophenyl)methacrylamide (MPMA), bis(2-methacryloyloxyethyl) disulfide (BMEDS), bis(5-methacryloyloxypentyl) disulfide (BMPDS) and bis(10-methacryloyloxydecyl) disulfide (BMDDS) were synthesized in accordance with the teachings of the relevant publications. Primers, each in the form of a 5% acetone solution of respective compound, were prepared according to EXAMPLE 8.

For evaluation of adhesion performance relative to precious metals by using the respective primers obtained, tests were made in the same way as in EXAMPLE 8, except that poly(methyl methacrylate) (PMMA) and methyl methacrylate (MMA) were used as adhesive resins, and that as polymerization catalysts were used benzoyl peroxide (BPO) and N, N-di(2-hydroxyethyl)-p-toluidine (DEPT); MMA-PMMA/BPO-DEPT system resins. The results are shown in Table 2.

TABLE 2

Metal-Metal Tensile Bond Strength (kgf/cm²) in 2000-Time Thermal Cycle Tests: BPO-DEPT System

|  | EXAMPLE 15 (2-MEDT) | COMPARATIVE EXAMPLE 3 (4-META) | COMPARATIVE EXAMPLE 4 (VBATDT) | COMPARATIVE EXAMPLE 5 (MPMA) | COMPARATIVE EXAMPLE 6 (BMEDS) | COMPARATIVE EXAMPLE 7 (BMPDS) | COMPARATIVE EXAMPLE 8 (BMDDS) |
|---|---|---|---|---|---|---|---|
| Gold | 196 | 0 | 69 | 16 | 0 | 64 | 66 |
| Silver | 396 | 0 | 0 | 0 | 0 | 0 | 0 |
| Platinum | 338 | 0 | 149 | 5 | 222 | 354 | 351 |
| Palladium | 193 | 27 | 100 | 70 | 118 | 215 | 217 |
| Gold alloy | 412 | 0 | 263 | 38 | 236 | 288 | 368 |
| Silver alloy | 396 | 105 | 257 | 218 | 106 | 140 | 289 |
| Gold/silver/palladium alloy | 451 | 158 | 281 | 115 | 246 | 244 | 332 |

Notes:
Adhesive resins used: MMA—PMMA/BPO-DEPT resin system.
Precious metals: all in pure state; alloys used: alloys for dental
Gold alloy: "Casting Gold M. C." (type IV) (made by GC K. K.)
Silver alloy: "Sunsilver C. B." (made by Sankin K. K.)
Gold/silver/palladium alloy: "Castwell M. C." (made by GC K. K.)

As is apparent from Table 2 results, 2-MEDT, a compound of the invention, when used in conjunction with general-purpose catalyst BPO-DEPT, exhibits exceedingly higher bond durability and greater storage stability as compared with conventional compounds, such as 4-META, VBATDT, MPMA, BMEDS and BMPDS.

In contrast, it has now been found that the performance of MPMA is very low in bond durability as well as in storage stability. It has also been made clear that VBATDT, BMEDS and BMPDS have a deficiency in respect of bond durability such that its adhesion performance relative to gold and silver in particular is noticeably low.

It may be noted that 10-methacryloyloxydecyl dihydrogen thiophosphate, a thiophosphoric compound, was omitted from evaluation for bond performance, because the compound has unacceptably low shelf stability and tends to generate extremely bad smell, which is a problem from the standpoint of practical use irrespective of whether or not the compound deserves such evaluation.

It has now been found that in contrast to such straight-chain disulfide compound, compounds of the invention which incorporate a cyclic disulfide compound exhibit stable and much higher bond durability in relation to gold, silver and alloys thereof.

With reference to the low bond performance of bis(methacryloylalkyl) disulfide used in combination with BPO-DEPT catalysts as in COMPARATIVE EXAMPLES 6–8, it may be noted that reports to that effect were made by the present inventors in "Dental Material & Equipment", vol. 11, "Lecture Issue 20", pp 234–235 (1992), and also in "Dental Material & Equipment", vol. 12, "Lecture Issue 21", pp 164–165 (1993).

EXAMPLE 16–18 AND COMPARATIVE EXAMPLE 9

Tests of enamel-gold alloy bond strength under shear were carried out by using primer compounds of EXAMPLES 8–10 and adhesive resin cements of BPO-DEPT-barbituric acid derivative system.

An adhesive resin cement powder was prepared by mixing silane-treated silica (75 parts by weight), silane-treated barium sulfate (25 parts by weight), N, N-di(2-hydroxyethyl)-p-toluidine (0.1 part by weight) and 1-benzyl-5-phenyl barbituric acid (1.0 part by weight).

A liquid adhesive resin cement was prepared by mixing a 1:2 (mol) reaction product of 2, 2, 4-trimethylhexamethylene diisocyanate and 2-hydroxyethyl methacrylate (65 parts by weight), triethyleneglycol dimethacrylate (20 parts by weight), ethyleneglycol dimethacrylate (10 parts by weight), 4-acryloxyethyl trimellitic acid (5.0 parts by weight), benzoyl peroxide (0.5 part by weight), and butylated hydroxytoluene (0.05 part by weight).

In conduct of tests, a bovine tooth was embedded in an epoxy resin, and then enamel surface of the tooth was exposed, which was then abrasively polished with waterproof sand paper No. #600 under water pouring. After drying, the enamel surface was subjected to etching with phosphoric acid for 30 seconds, followed by water washing and drying.

A type IV gold alloy of 4 mm diameter and 2 mm height ("Supergold" (type 4): made by Shofu Inc.) was sand-blasted over its adhesion surface with aluminum oxide particles, and was then ultrasonically cleaned in water, followed by drying.

A metal surface to be treated was coated with the primers prepared in EXAMPLE 1–3, followed by air drying. Thereafter, the foregoing powder and liquid adhesive resin cements were mixed in a powder-liquid ratio of 3.5:1.0 (weight ratio) and kneaded into paste, with which paste the enamel surface and the gold alloy surface were bonded to each other.

Further, 2000-time thermal cycle tests were carried out in the same way as in EXAMPLE 8, and thereafter the compressive shear bond strength was measured at a crosshead speed of 1 mm/min.

For comparison purposes, samples with which no primer treatment was made were tested in the same way as above described. The results of the foregoing tests are shown in Table 3.

TABLE 3

Enamel-Gold Alloy Shear Bond Strength (kgf/cm²) in 2000-Time Thermal Cycle Tests; Barbituric Acid Type

|  | Adhesive monomer in primer | Enamel-gold alloy shear bond strength (kgf/cm²) (2000 cycles) |
|---|---|---|
| EXAMPLE 16 | 2-MEDT | 305 |
| EXAMPLE 17 | 6-MHDT | 338 |

TABLE 3-continued

Enamel-Gold Alloy Shear Bond Strength (kgf/cm²) in 2000-Time Thermal Cycle Tests; Barbituric Acid Type

| | Adhesive monomer in primer | Enamel-gold alloy shear bond strength (kgf/cm²) (2000 cycles) |
|---|---|---|
| EXAMPLE 18 | 10-MDDT | 317 |
| COMPARATIVE EXAMPLE 9 | No primer | 165 |

Notes:
Adhesive resins used: BPO-DEPT-barbituric resin system.
Gold alloy: "Supergold" (type 4) (made by "Shofu Inc.")

EXAMPLE 19

Powder and liquid adhesive resin cements incorporating compounds of the invention were prepared in the following way. For the powder resin cement, the powder cement of EXAMPLE 16 was used as such. The liquid resin cement was prepared by mixing a 1:2 (mol) reaction product of isophorone diisocyanate and 2-hydroxyethyl methacrylate (65 parts by weight), triethylene glycol dimethacrylate (24 parts by weight), ethyleneglycol dimethacrylate (10 parts by weight), 6-methacryloyl-oxyhexyl 6, 8-dithiooctanate (6-MHDT) (1.0 part by weight), benzoyl peroxide (0.5 part by weight) and butylated hydroxytoluene (0.05 part by weight).

When the powder and liquid adhesive resin cements were mixed and kneaded in a powder/liquid ratio of 3.5:1.0 (weight ratio), the resulting paste was hardened in 5 to 8 minutes at room temperature. An enamel-gold alloy bond was formed using the paste, and in the same way as in EXAMPLE 16 the shear strength of the bond was measured to give 287 kgf/cm².

EXAMPLE 20

Into a four-necked 500 ml flask were introduced 18.90 g (0.07 mol) of 12-hydroxydodecyl methacrylate synthesized from 1, 12-dodecamethylene glycol and methacrylic acid in substantially the same way as in EXAMPLE 3, 10.30 g (0.05 mol) of N, N'-dicyclohexylcarbodiimide, 10.36 g (0.05 mol) of thioctic acid and 100 g of benzene, which were dissolved therein, and the solution was continuously stirred at room temperature for two weeks. There developed a white precipitate. After completion of the reaction step, the precipitate was filtered. Subsequently, the step of separation and purification was carried out in the same manner as in EXAMPLE 1. Then the benzene was distilled away. Thus, an object compound in a yellow crystalline form was obtained in the amount of 7.55 g (yield: 23.5%). The compound had a melting point of 30.3° to 30.6° C.

Analyses of the compound, including $^1$H-NMR spectral analysis, $^{13}$C-NMR spectral analysis and mass spectral analysis, were carried out. As a result, the compound was identified as 12-methacryloyloxydodecyl 6, 8-dithiooctanate (referred to as 12-MDDDT) represented by the following formula.

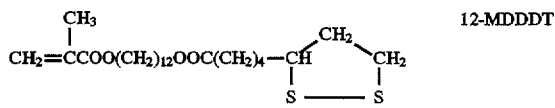

12-MDDDT $^1$H-NMR spectrum:(ppm)

| 1.27 | (16H —O—CH₂CH₂—(C$\underline{H}$₂)₈—CH₂CH₂—)— ) |
|---|---|
| 1.44 | (4H—O—CH₂C$\underline{H}$₂—(CH₂)₈—C$\underline{H}$₂CH₂—O—) |
| 1.27, 1.65, 2.31, 3.14 | (8H—OOC-13 (C$\underline{H}$₂)₄—CH<) |
| 1.94 | (3H—CH₃) |
| 1.65, 1.91, 2.46, 3.55 | (5H>C$\underline{H}$—C$\underline{H}$₂—C$\underline{H}$₂) |
| 4.06, 4.13 | (4H—O—C$\underline{H}$₂CH₂—(CH₂)₈—CH₂C$\underline{H}$₂—O—) |
| 5.54, 6.09 | (2H C$\underline{H}$₂lC<) |

$^{13}$C-NMR spectrum:(ppm)

| 18.2 | (1C —$\underline{C}$H₃) |
|---|---|
| 24.6, 28.6, 33.9, 34.4 | (4C —OO$\underline{C}$—(CH₂)₄—) |
| 38.3, 40.0, 56.2 | (3C >$\underline{C}$H—$\underline{C}$H₂—$\underline{C}$H₂—) |
| 25.8, 28.4, 28.5, 28.6, 29.1, 29.3, 64.3, 64.6 | (12C —O—($\underline{C}$H₂)₁₂—O—) |
| 124.9, 136.4 | (2C CH₂=$\underline{C}$—) |
| 167.3, 173.3 | (2C —$\underline{C}$OO—(CH₂)₁₂—OO$\underline{C}$—) |

MASS spectrum:molecular weight 458

Metal-metal tensile bond strength measurements were made using 12-methacryloyloxydodecyl 6, 8-dithiooctanate (12-MDDDT) in substantially the same way as in EXAMPLE 1. The results of the measurements are shown in Table 4.

TABLE 4

Precious Metal-Precious Metal Tensile Bond Strength (kgf/cm²)2,000-Time Thermal cycles: TBBO resin system

| Substrate metal | EXAMPLE 20 (12-MDDDT) |
|---|---|
| Gold | 259 |
| Silver | 440 |
| Platinum | 488 |
| Palladium | 499 |
| Gold alloy | 505 |
| Silver alloy | 391 |
| Gold/silver/palladium alloy | 445 |

Novel adhesive compositions according to the present invention which incorporate a (meth)acrylic ester derivative containing a disulfide cyclic group exhibit strong adhesion and high bond durability relative to precious metals, such as gold, silver, platinum, palladium and alloys thereof.

Such (meth)acrylic ester derivatives and adhesives incorporating any such derivative are available for use as adhesives for precious metals in dental and medical application areas and, in addition, may be widely used as general industrial adhesives in general industrial fields including jewelry art.

What is claimed is:

1. A (meth)acrylic ester having a disulfide cyclic group represented by formula (I):

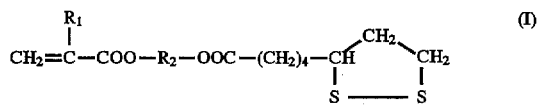

in which R₁ represents a hydrogen atom or methyl group, and R₂ represents a C₃-C₁₄ alkylene group unsubstituted or substituted by a member selected from the group consisting of an unsaturated group, an alkyl group, and an alkylene group bonded with phenoxy group.

2. A (meth)acrylic ester of claim 1, in which the unsaturated group is a group of the formula:

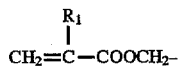
wherein $R_1$ is a hydrogen atom or a methyl group.
3. A (meth)acrylic ester of claim 1, in which the alkyl group is methyl or ethyl.
4. A (meth)acrylic ester of claim 1, in which the alkylene group bonded with a phenoxy group is phenoxy ethylene.
5. A (meth)acrylic ester of claim 1 in which $R_2$ is unsubstituted $C_3$–$C_{14}$ alkylene group.
* * * * *